(12) United States Patent
Johnson et al.

(10) Patent No.: US 7,591,802 B2
(45) Date of Patent: Sep. 22, 2009

(54) SEAL HOUSING HAVING ANTI-INVERSION FEATURES

(75) Inventors: Gary M. Johnson, Mission Viejo, CA (US); Jeremy J. Albrecht, Ladera Ranch, CA (US); Nabil Hilal, Laguna Niguel, CA (US); Charles C. Hart, Summerville, SC (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 798 days.

(21) Appl. No.: 11/119,189

(22) Filed: Apr. 29, 2005

(65) Prior Publication Data

US 2006/0264991 A1 Nov. 23, 2006

(51) Int. Cl.
*A61M 5/178* (2006.01)
(52) U.S. Cl. .................................. 604/167.06
(58) Field of Classification Search .................. 606/185, 606/186; 604/30, 31, 34, 167.01–167.04, 604/167.06, 196, 246, 256, 278
See application file for complete search history.

(56) References Cited

U.S. PATENT DOCUMENTS 4,414,973 A 11/1983 Matheson et al.

(Continued)

FOREIGN PATENT DOCUMENTS

WO WO 94/07552 4/1994

OTHER PUBLICATIONS

European Patent Office, The International Search Report and The Written Opinion for International Patent Application No. PCT/US2006/007347, mailed May 26, 2006, 11 pages.

International Publication No. WO 94/07552 for International Application No. PCT/US93/09067, Apr. 14, 1994, Applied Medical Resources Corporation.

(Continued)

*Primary Examiner*—Nicholas D Lucchesi
*Assistant Examiner*—Nathan R Price
(74) *Attorney, Agent, or Firm*—John F. Heal; Patrick Y. Ikehara; Kenneth V. Vu (57) ABSTRACT

The invention is directed to a trocar adapted to form a seal around a surgical instrument, the trocar comprising a cannula having an axis extending between a proximal end and a distal end; a housing having a proximal wall and forming with the cannula a working channel sized and configured to receive the instrument; a septum seal disposed in the housing and extending transverse to the axis of the cannula across the working channel, the septum seal having a normal state when the instrument is absent from the working channel and a stretched state when the instrument is being withdrawn from the working channel; portions of the proximal wall of the housing defining an orifice sized and configured to receive the instrument into the working channel; and an elastomeric ring-shaped projection extending axially distally between the proximal wall and the septum seal, the ring-shaped projection having an axial length adapted to deform to prevent inversion and binding of the septum seal and the orifice upon withdrawal of the surgical instrument. In particular, the septum seal is prevented from reaching the orifice in the proximal wall of the housing when the instrument is withdrawn. The projection may be bonded, insert-molded, or compressively fitted to the proximal wall of the housing. The projection may be formed of an elastomeric material such as natural or synthetic rubber. The projection may further comprise a plurality of portions or fingers extending axially distally from the proximal wall, each of the extending portions or fingers may further include a living hinge. In another aspect, the ring-shaped projection may be formed on the surface of the septum seal instead of the proximal wall of the housing. That is, the ring-shaped projection may be formed to extend axially proximally from the surface of the septum seal toward the proximal wall of the housing.

20 Claims, 11 Drawing Sheets

U.S. PATENT DOCUMENTS

| | | | |
|---|---|---|---|
| 4,535,819 A | 8/1985 | Atkinson et al. |
| 4,566,812 A | 1/1986 | Takei et al. |
| 4,645,494 A | 2/1987 | Lee et al. |
| 4,655,752 A | 4/1987 | Honkanen et al. |
| 4,655,765 A | 4/1987 | Swift |
| 4,658,852 A | 4/1987 | Weingarten |
| 4,744,571 A | 5/1988 | Geberth, Jr. |
| 4,762,517 A | 8/1988 | McIntyre et al. |
| 4,765,588 A | 8/1988 | Atkinson |
| 4,773,552 A | 9/1988 | Boege et al. |
| 4,781,680 A | 11/1988 | Redmond et al. |
| 4,827,973 A | 5/1989 | Boehmer |
| 4,929,235 A | 5/1990 | Merry et al. |
| 4,960,412 A | 10/1990 | Fink |
| 5,004,123 A | 4/1991 | Stoody |
| 5,022,634 A | 6/1991 | Keeble |
| 5,026,324 A | 6/1991 | Schurger et al. |
| 5,106,054 A | 4/1992 | Mollenauer et al. |
| 5,127,626 A | 7/1992 | Hilal et al. |
| 5,141,498 A | 8/1992 | Christian |
| 5,180,373 A | 1/1993 | Green et al. |
| 5,197,955 A | 3/1993 | Stephens et al. |
| 5,242,412 A | 9/1993 | Blake, III |
| 5,295,658 A | 3/1994 | Atkinson et al. |
| 5,308,336 A | 5/1994 | Hart et al. |
| 5,330,437 A | 7/1994 | Durman |
| 5,342,315 A | 8/1994 | Rowe et al. |
| 5,342,316 A | 8/1994 | Wallace |
| 5,360,417 A | 11/1994 | Gravener et al. |
| 5,385,552 A | 1/1995 | Haber et al. |
| 5,407,434 A | 4/1995 | Gross |
| 5,443,452 A | 8/1995 | Hart et al. |
| 5,496,280 A | 3/1996 | Vandenbroek et al. |
| 5,545,142 A | 8/1996 | Stephens et al. |
| 5,584,850 A | 12/1996 | Hart et al. |
| 5,709,664 A | 1/1998 | Vandenbroek et al. |
| 5,827,228 A | 10/1998 | Rowe |
| 5,906,595 A | 5/1999 | Powell et al. |
| 6,860,869 B2 | 3/2005 | Dennis |
| 2005/0065475 A1 | 3/2005 | Hart et al. |

OTHER PUBLICATIONS

Paul R. Beninger, M.D., Department of Health & Human Services, Food and Drug Administration, correspondence, Oct. 12, 1993.

The International Bureau of WIPO, International Preliminary Report on Patentability for International Application No. PCT/US2006/007347 mailed Nov. 8, 2007.

SEAL HOUSING HAVING ANTI-INVERSION FEATURES

BACKGROUND OF THE INVENTION

1. Field of the Invention

This invention generally relates to access devices that provide working channels through a body wall and into a body cavity and, more particularly, to instrument seals in laparoscopic trocars.

2. Discussion of Related Art

Less invasive abdominal surgery, commonly referred to as laparoscopic surgery, is undertaken with instruments extending across the abdominal wall. With this procedure, the volume of the abdominal surgical site is increased by inflating the abdomen with gas. In order to maintain the pressure of the gas within the abdomen while passing instruments across the abdominal wall, access devices such as trocars, are positioned through holes in the abdomen. These trocars are provided with seals which engage the instruments as they are passed through the trocars and into the inflated abdomen. That is, in addition to providing a pathway for surgical instruments, the trocar is used to communicate a pressurized gas flow into an abdominal cavity so that the body cavity is expanded under a positive gas pressure.

The trocar, therefore, must have a combination of seal members that prevent gas from escaping the abdominal cavity. It is important that the gas pressure be maintained at a constant pressure and volume. Generally, the trocar comprises a cannula that traverses the abdominal wall and a seal housing that contains the requisite seals. Typically, a common seal arrangement comprises a first seal sized and configured to serve as a check valve when there is no instrument within the working channel of the trocar, and a second or septum seal sized and configured to seal around an inserted instrument.

The seals associated with the trocar are unique in that they must be very dependable, durable, unobtrusive and respond to a wide variety of instrument sizes and shapes. In particular, the seals should not interfere with or compromise the use of delicate surgical instruments, nor should the seals cause unwanted restriction or movement of an instrument. For example, an instrument must remain where it is placed. Furthermore, the seal must allow an instrument to move in, out and around the working channel and in a direction that remains as closely as possible to the wishes of the user. As such, there are many competing requirements in the construction of trocar seals.

In one example, a septum seal that is made of a very thin, resilient, durable material may have a tendency to leak as an instrument is moved from side to side within the working channel of the trocar. That is, the center opening or orifice of the septum seal may subsequently elongate as an instrument moves from side to side, causing a gas leak. To prevent this condition, the orifice of the septum seal may be reduced to a minimum. This arrangement, however, presents a problem when it is being used with a large instrument as it may draw the seal back into the orifice during withdrawal of the instrument from the trocar, causing the seal to invert and therefore binding between the instrument and orifice. This problem is addressed in Applicant's U.S. Pat. No. 5,584,850, which discloses an anti-inversion seal and which is incorporated herein by reference.

The anti-inversion seal of the '850 patent has proven to be effective in preventing the seal to invert and binding between an instrument and the orifice. Nevertheless, there remains a need in the art to improve the anti-inversion seals so as to make them more responsive to an increasing variety of instruments.

SUMMARY OF THE INVENTION

The invention is directed to a trocar adapted to form a seal around a surgical instrument, the trocar comprising a cannula having an axis extending between a proximal end and a distal end; a housing having a proximal wall and forming with the cannula a working channel sized and configured to receive the instrument; a septum seal disposed in the housing and extending transverse to the axis of the cannula across the working channel, the septum seal having a normal state when the instrument is absent from the working channel and a stretched state when the instrument is being withdrawn from the working channel; portions of the proximal wall of the housing defining an orifice sized and configured to receive the instrument into the working channel; and an elastomeric ring-shaped projection extending axially distally between the proximal wall and the septum seal, the ring-shaped projection having an axial length adapted to deform to prevent inversion and binding of the septum seal and the orifice upon withdrawal of the surgical instrument. With the trocar of the invention, the septum seal is prevented from reaching the orifice in the proximal wall of the housing when the instrument is withdrawn. The trocar may further comprise a zero closure valve, such as a double duck-bill valve, disposed in the housing distally of the septum seal. The ring-shaped projection may be bonded, insert-molded, or compressively fitted to the proximal wall of the housing. The housing may be formed of a rigid material, and the projection may be formed of a soft or elastomeric material such as natural or synthetic rubber. For example, the projection may be formed of an elastomeric material including at least one of gel, silicone, soft thermoplastics, polyvinyl chloride (PVC), urethane, thermoplastic elastomers, Kraton®, latex, pellethane, monoprene, neoprene, and polyisoprene. It is appreciated that the elastomeric material of the ring-shaped projection prevents excessive wear on the septum seal. Furthermore, the ring-shaped projection of the invention facilitates the over-center positioning of the septum seal during insertion and removal of the surgical instrument.

In another aspect, the trocar may further comprise a ring transversely formed between the septum seal and the proximal wall, the ring being attached to the ring-shaped projection. The projection may further comprise a plurality of portions or fingers extending axially distally from the proximal wall, wherein each of the extending portions or fingers bends or deforms in accordance with movement of the surgical instrument. With this aspect, each of the extending portions or fingers may further include a living hinge.

In yet another aspect, the invention is directed to a trocar adapted to form a seal around a surgical instrument, the trocar comprising a cannula having an axis extending between a proximal end and a distal end; a housing having a proximal wall and forming with the cannula a working channel sized and configured to receive the instrument; a septum seal disposed in the housing and extending transverse to the axis of the cannula across the working channel, the septum seal having a surface opposing the proximal wall of the housing, the septum seal having a normal state when the instrument is absent from the working channel and a stretched state when the instrument is being withdrawn from the working channel; portions of the proximal wall of the housing defining an orifice sized and configured to receive the instrument into the working channel; and an elastomeric ring-shaped projection extending axially proximally from the surface toward the proximal wall of the housing, the ring-shaped projection having an axial length adapted to deform to prevent inversion and binding of the septum seal and the orifice upon withdrawal of the surgical instrument. This aspect is similar with the first aspect except the ring-shaped projection is formed on the surface of the septum seal instead of the wall of the housing. That is, the ring-shaped projection may be formed to either extend axially distally from the proximal wall of the housing toward the septum seal or to extend axially proximally from the surface of the septum seal toward the proximal wall of the housing.

These and other features of the invention will become more apparent with a discussion of the various embodiments in reference to the associated drawings.

DESCRIPTION OF THE DRAWINGS

The accompanying drawings, which are included in and constitute a part of this specification, illustrate the embodiments of the invention and, together with the description, explain the features and principles of the invention. In the drawings.

DESCRIPTION OF THE INVENTION

Figure 1:
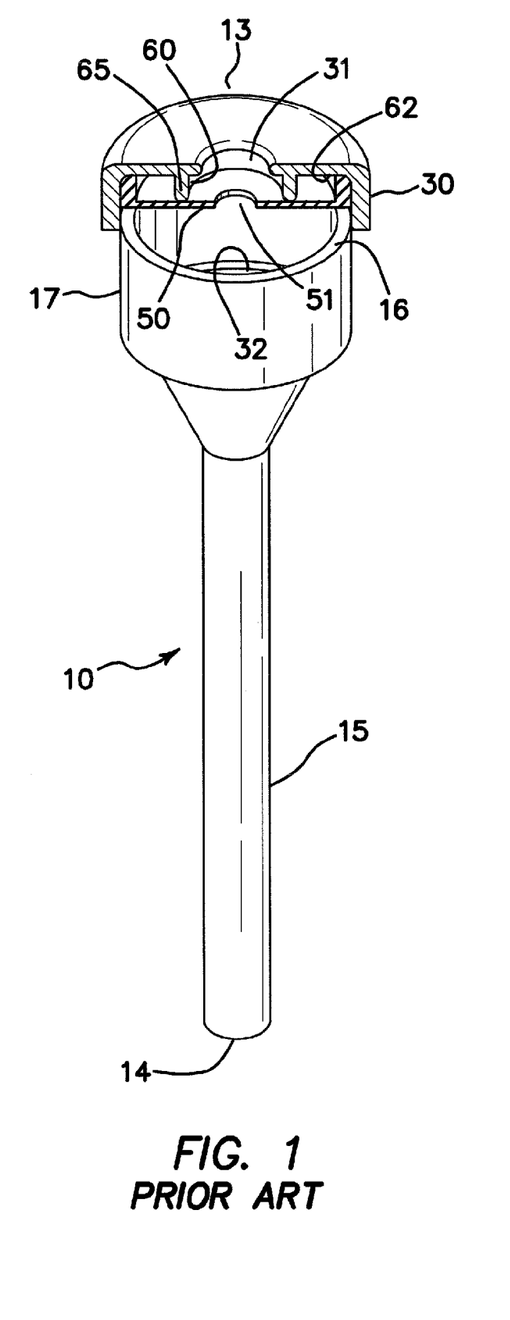
FIG. 1 is a perspective section view of a trocar according to the prior art.
Figure 2:
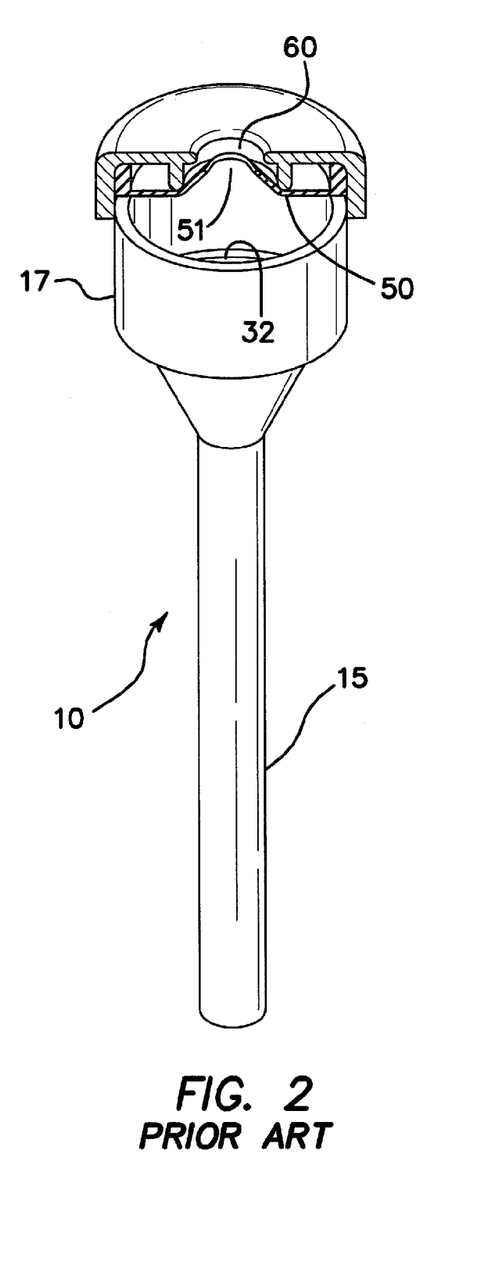
FIG. 2 illustrates the septum seal of the trocar of FIG. 1 when an instrument is within the working channel of the trocar.
Figure 3:
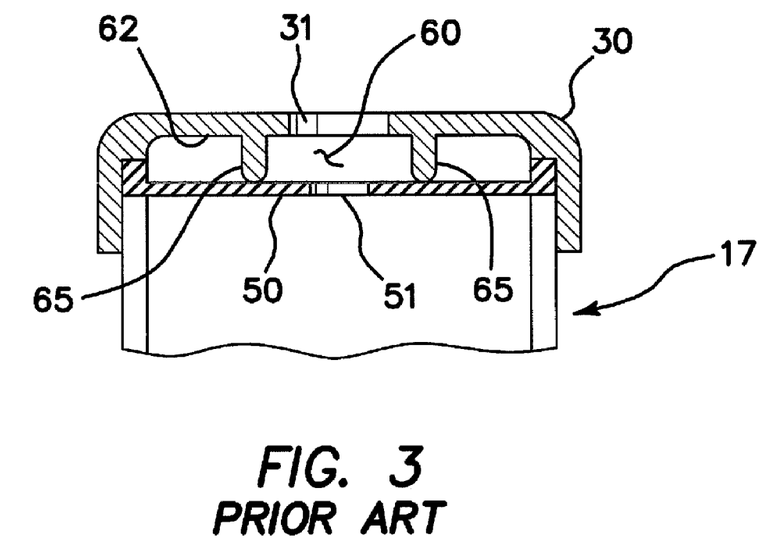
FIG. 3 illustrates a side-section view of a housing of the trocar of FIG. 1 with no instrument in the working channel and the septum seal in a relaxed condition.
Figure 4:
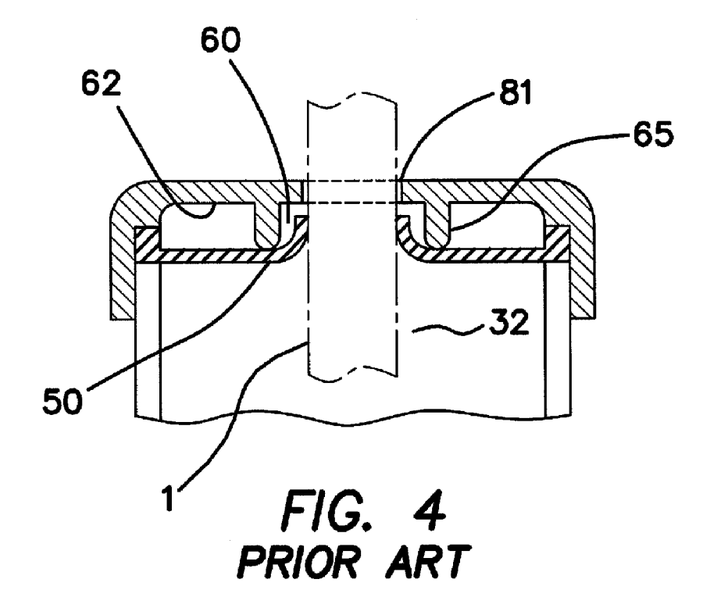
FIG. 4 illustrates a side-section view of the housing of the trocar of FIG. 1 with an instrument in the working channel and the septum seal in a stretched condition.
Figure 5:
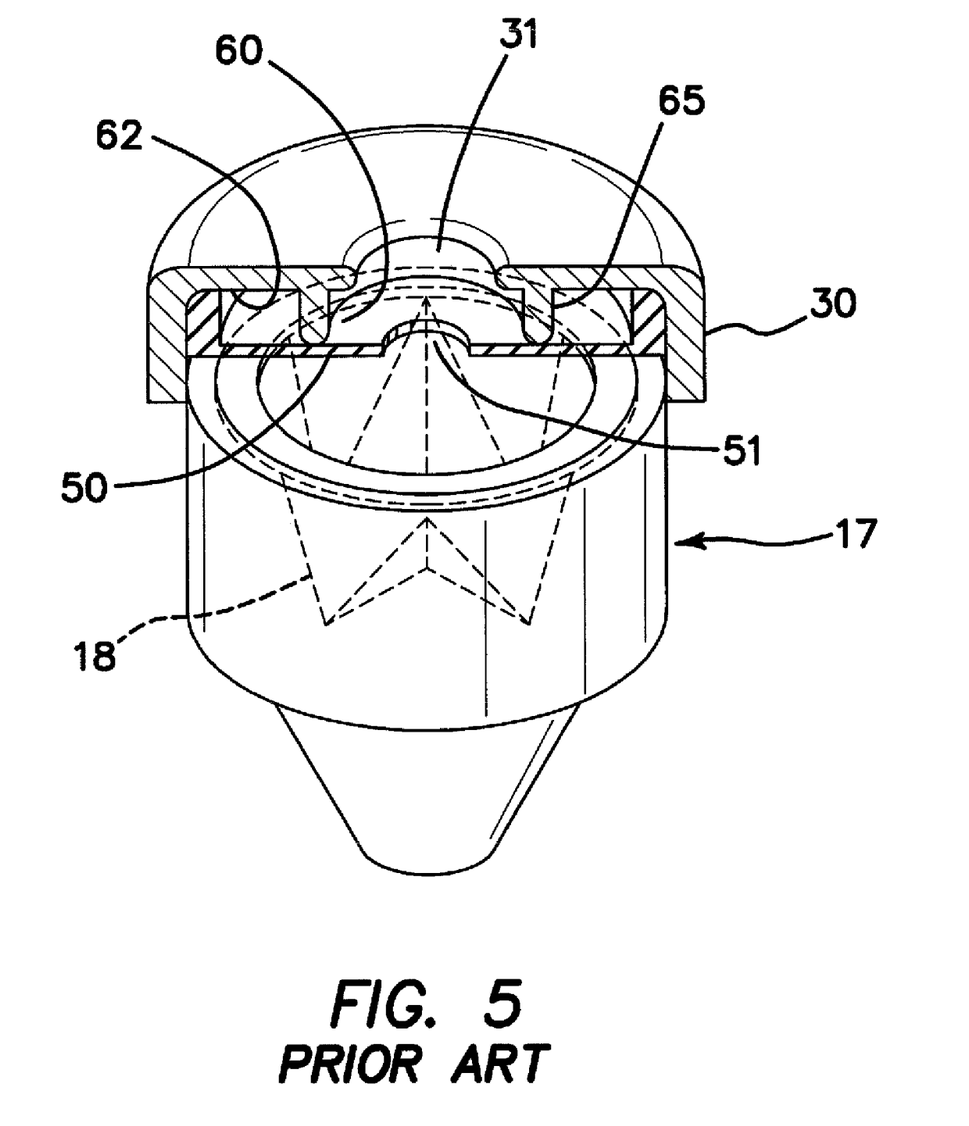
FIG. 5 is a perspective section view of a trocar housing including a duckbill valve according to the prior art.
Figure 6:
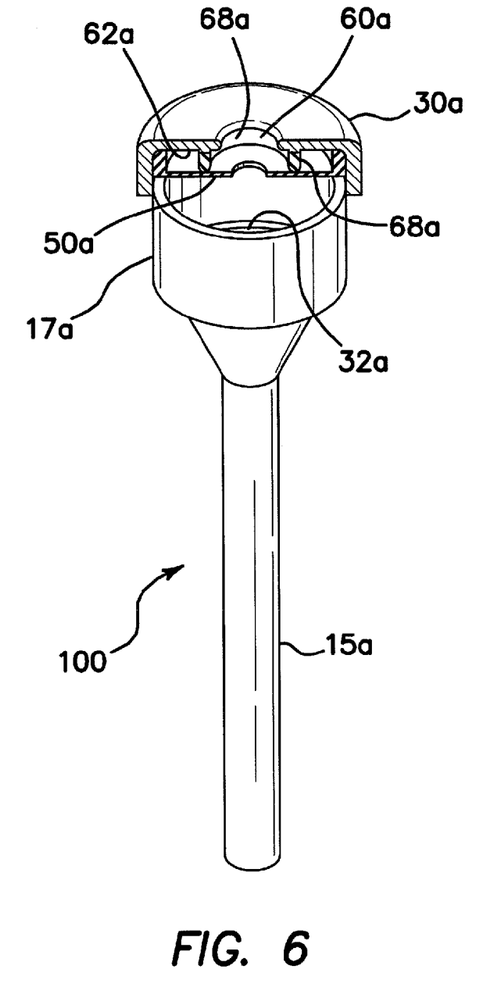
FIG. 6 is a perspective section view of a trocar according to an embodiment of the invention.

Referring to FIGS. 1-4, there is shown a surgical access device 10 of the prior art having a proximal end 13 and a distal end 14 comprising a cannula 15 and a seal housing 17 operatively connected to a proximal end of the cannula 15 to form a seal around a surgical instrument inserted through the surgical access device 10. The seal housing 17 further comprises a seal-housing cap 30 operatively connected at the proximal end of the seal housing 17 and a septum seal 50 to maintain a fluid tight barrier when an instrument 1 is inserted within a working channel 32 of the access device 10 as further described below. The cannula 15 is sized and configured to provide access through a body wall and into a body cavity. Referring to FIG. 5, the septum seal 50 can be used in combination with an elastomeric zero-closure valve 18 that is commonly referred to as a duck-bill valve. The zero-closure valve 18 and septum seal 50 function to form seals across the working channel 32; however, they perform this function at different times and in different ways. The zero-closure valve 18 forms its seal across the working channel 32 in the absence of an instrument while the septum seal 50 forms its seal across the working channel 32 in the presence of an instrument.

The septum seal 50 typically comprises an elastomeric disc that is sized and configured to fit within the seal housing 17 or cap 30 in a fluid-tight relationship and includes a seal center orifice 51 having a diameter appropriate for use with a specific range of instruments to be used there-through. The cap 30 also has a cap center orifice 31 that aligns an incoming instrument with the seal center orifice 51. The cap center orifice 31 operates to provide an appropriate restriction against side-to-side motion that could otherwise elongate the seal center orifice 51. The cap center orifice 31 is therefore sized to the designated range of instruments for use with the access device 10 as shown, for example, in FIGS. 3 and 4.

The seal center orifice 51 is generally smaller than the cap center orifice 31 and subsequently forms a fluid tight seal with the inserted instrument 1 within the working channel 32 of the access device 10. An annular ring-shaped projection 65 is provided which extends axially distally from a proximal wall 62 of the seal housing 17 or cap 30 to create an annular recess 60. The projection 65 provides sufficient distance between the septum seal 50 and the cap center orifice 31 such that the septum seal 50 material is prevented from binding the cap center orifice 31 when the instrument 1 is being withdrawn from the access device 10.

Referring now to FIGS. 6-10, there is shown a surgical access device 100 of the invention wherein elements of structures similar to those previously discussed are designated by the same reference numeral followed by the lower case letter "a". The access device 100 comprises a cannula 15a and a seal housing 17a operatively connected to a proximal end of the cannula 15a to form a seal around a surgical instrument inserted through the surgical access device 100. The seal housing 17a further comprises a seal-housing cap 30a operatively attached at the proximal end of the seal housing 17a and a septum seal 50a to maintain a fluid tight barrier when an instrument 1a is inserted within a working channel 32a of the access device 100. The seal-housing cap 30a further includes a cap center orifice 31a and a ring-shaped projection 68a extending axially distally from an inner wall 62a of cap 30a to create an annular recess 60a. A difference between the invention and the prior art is the projection 68a is not integrally formed with the wall 62a of the seal housing 17a or cap 30a. Instead, the projection 68a is bonded to or insert-molded with the wall 62a of the seal housing 17a or cap 30a as further described below. The ring-shaped projection 68a is constructed of an elastomeric material that is aligned with the cap center orifice 31a. The cap 30a is preferably formed of a rigid material, and the ring-shaped projection 68a is formed from an elastomeric material including at least one of polyisoprene, latex, silicone, neoprene, vinyl and the like. The hardness of the material may be adjusted to provide specific attributes.

Figure 8:
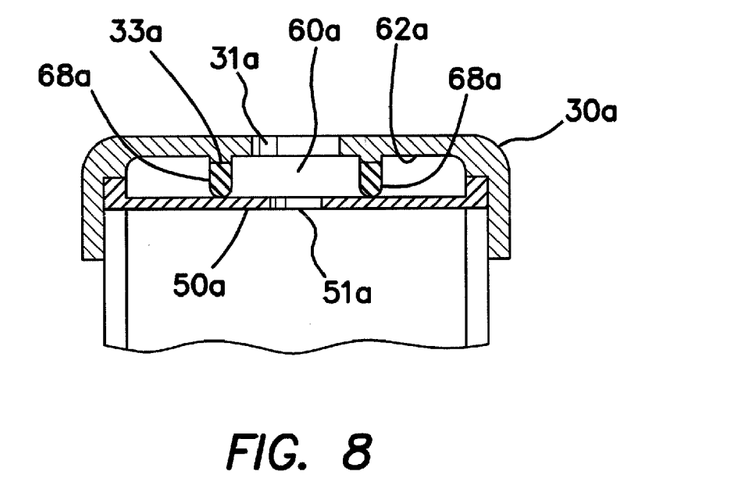
FIG. 8 illustrates a side-section view of a housing of the trocar of FIG. 6 with no instrument in the working channel and the septum seal in a relaxed condition.
Figure 9:
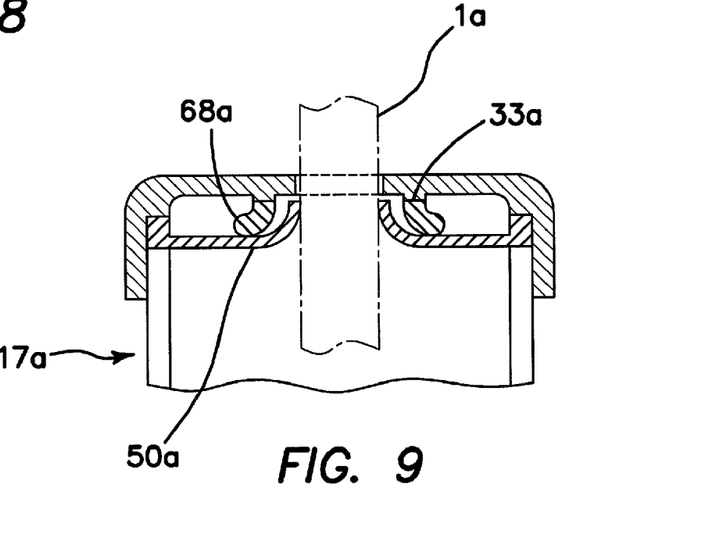
FIG. 9 illustrates a side-section view of the housing of the trocar of FIG. 6 with an instrument in the working channel and the septum seal in a stretched condition.
Figure 10:
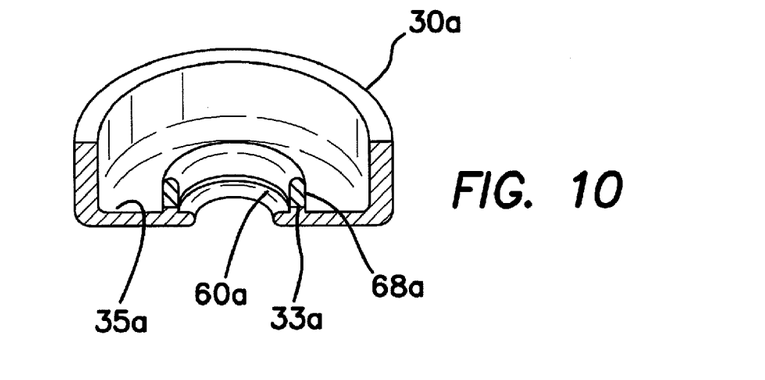
FIG. 10 is an inverted cut-away section view of a cap of FIG. 8.
Figure 11:
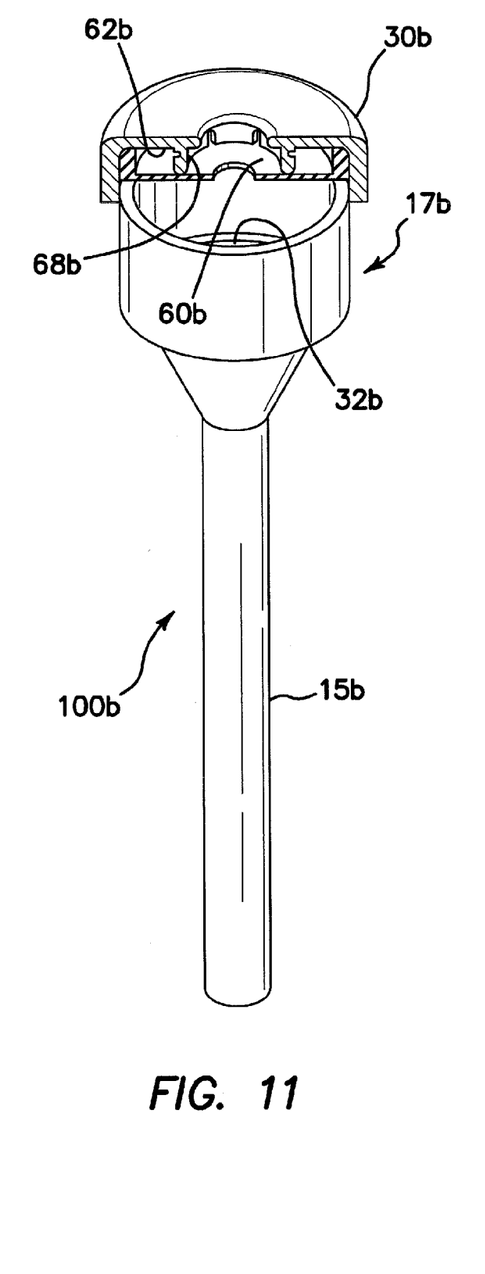
FIG. 11 is a perspective section view of a trocar according to another aspect of the invention having a plurality of flexible, elastomeric portions or fingers.
Figure 12:
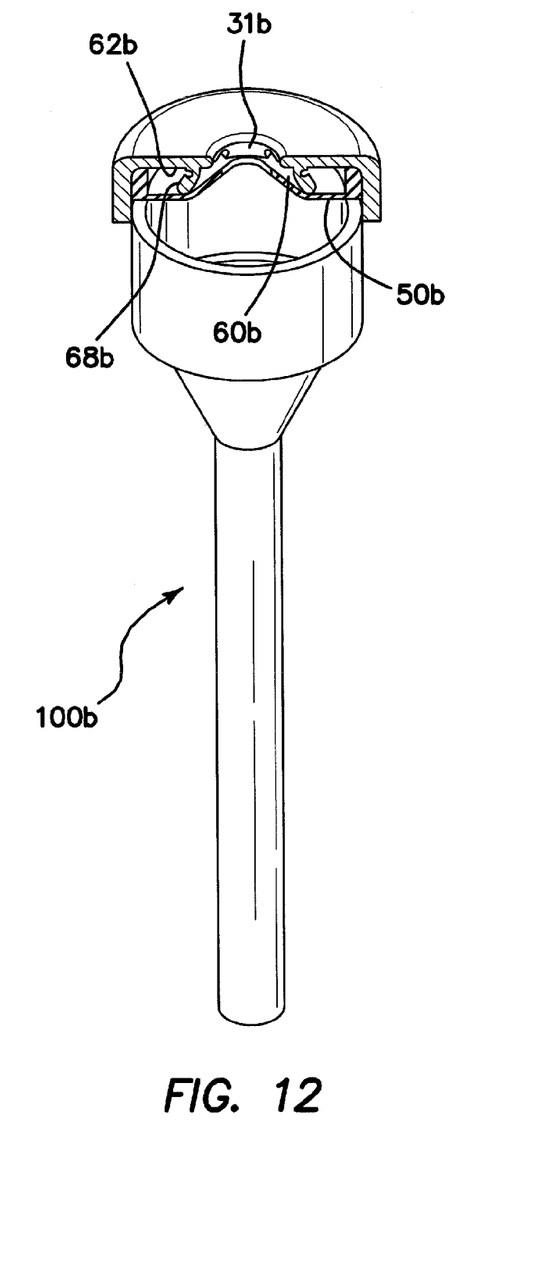
FIG. 12 illustrates the septum seal of the trocar of FIG. 11 when an instrument is within the working channel of the trocar.

Referring to FIGS. 8-10, the projection 68a may be bonded to a stand-off or holding feature 33a on cap 30a or it may be insert-molded with cap 30a. With this aspect, the projection 68a may be compressively fitted onto or into a holding feature 33a of cap 30a. In yet another aspect, the ring-shaped projection 68a may be formed as a separate piece that fits within the seal housing 17a or cap 30a, between the septum seal 50a and an inner surface of the seal housing 17a or cap 30a and is held in place by the assembled components.

Figure 7:
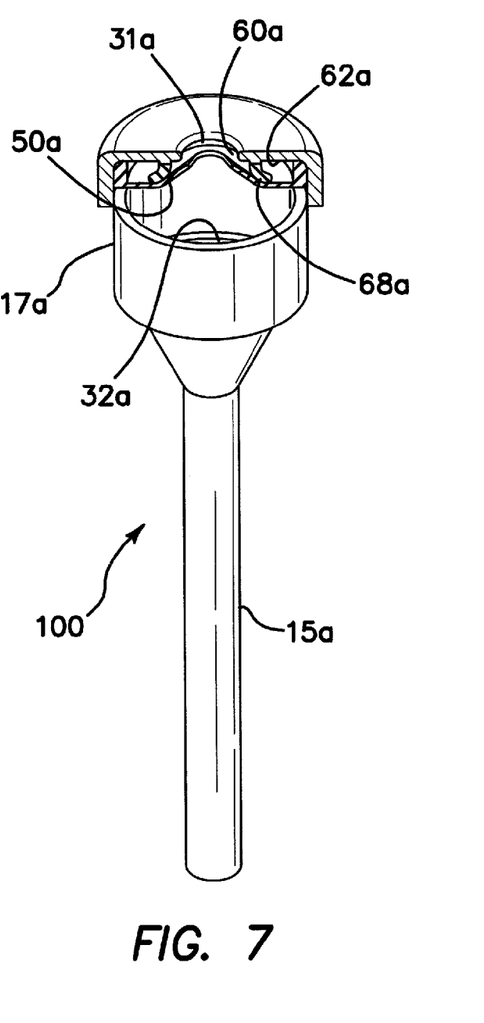
FIG. 7 illustrates the septum seal of the trocar of FIG. 6 when an instrument is within the working channel of the trocar.

During placement and removal of the instrument 1a, the elastomeric ring-shaped projection 68a may be deformed within the working channel 32a as illustrated in FIG. 7. The elastomeric material of the ring-shaped projection 68a prevents excessive wear or possible damage to the delicate septum seal 50a. Moreover, the elastomeric construction of the ring-shaped projection 68a further facilitates the over-center positioning of the septum seal 50a as the instrument 1a is being inserted or withdrawal from the access device 100 and as the instrument 1a transitions from a forward to a rearward condition. Stated another way, the ring-shaped projection 68a further serves to moderate the "oil-can" effect where a generally flat disc or septum seal is transitioned from a forward-tapered forward condition to a reverse-tapered condition. A detente condition of this type can cause an instrument within the working channel 32a to jump forward or rearward in response to the transition of the septum seal 50a from one condition to the other.

Figure 17:
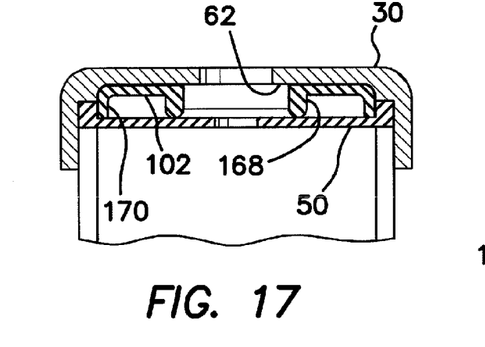
FIG. 17 illustrates a side-section view of a housing according to another aspect of the invention including a ring-shaped projection that is separately formed from the cap.
Figure 18:
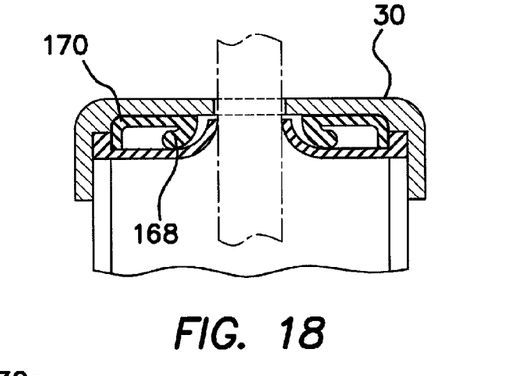
FIG. 18 illustrates a side-section view of the housing of FIG. 17 with an instrument in the working channel and with the septum seal in the stretched condition.

In another aspect of the invention as illustrated in FIGS. 17 and 18, a ring-shaped annular projection 168 may be formed separately to be located between the septum seal 50 and a proximal wall 62 of the cap 30. In particular, the ring-shaped projection 168 may further comprise a discrete and separate ring 102 to be assembled between the septum seal 50 and the proximal wall 62 of the cap 30. The ring 102 may cover most of the proximal wall 62 of the cap 30 and is glued, snap fit, or otherwise attached to the proximal wall 62 of cap 30. The ring 102 may further comprise a wall 170 along an outer diameter of the ring 102. It is appreciated that whether the projections 68a, 168 are formed as part of the cap or separately to be located between the septum seal and the cap, the projections 68a, 168 perform similar functions as described above.

Figure 13:
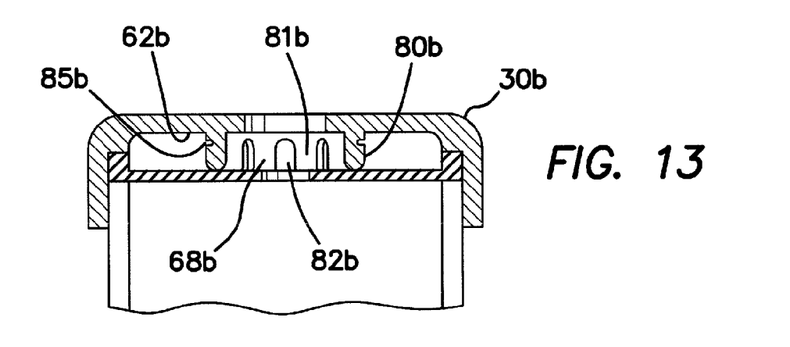
FIG. 13 illustrates a side-section view of a housing of the trocar of FIG. 11 with no instrument in the working channel and the septum seal in a relaxed condition.
Figure 14:
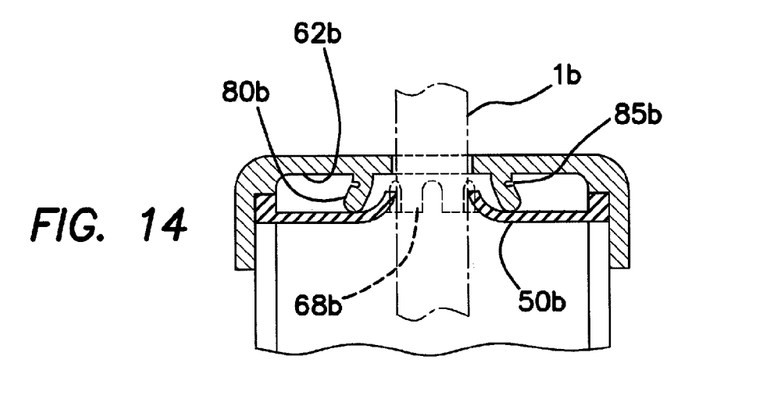
FIG. 14 illustrates a side-section view of the housing of the trocar of FIG. 11 with an instrument in the working channel and the septum seal in a stretched condition.
Figure 15:
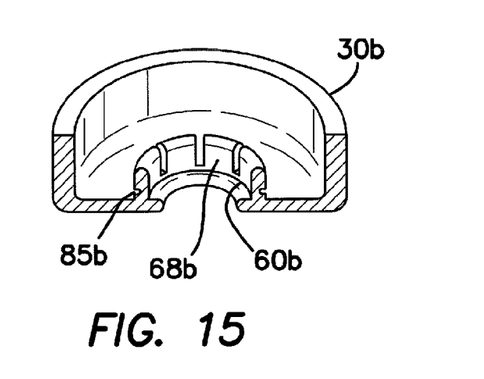
FIG. 15 is an inverted cut-away section view of a cap of FIG. 13.
Figure 16:
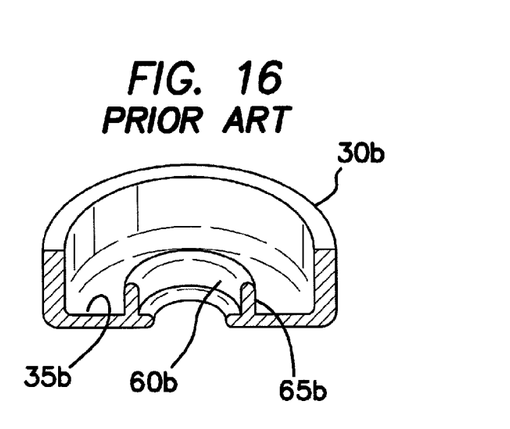
FIG. 16 is an inverted cut-away section view of a cap of the prior art having an elastomeric standoff ring.

Referring to FIGS. 11-15, there is shown a surgical access device 100b in accordance with another aspect of the invention. With this aspect, the surgical access device 100b comprises a cannula 15b and a seal housing 17b operatively connected to a proximal end of the cannula 15b to form a seal around a surgical instrument inserted through the surgical access device 100b. This aspect is similar to the previously described aspect in FIGS. 6-10 but further comprises a plurality of extending portions 81b or "fingers" that extend distally from wall surface 62b as illustrated in FIG. 13. Each of the extending portions 81b operates to bend or deform under the influence or movement of an instrument 1b placed within a working channel 32b of the access device 100b, and to bend or deform as the instrument 1b pulls the septum seal 50b into an annular recess 60b during withdrawal. Each portion or finger 81b may further include a living hinge 85b that allows the portion 81b to bend or deform and subsequently return to its original condition. Furthermore, the flexible construction of the portions 81b provide smooth operation of the surgical instrument 1b in the working channel 32b as the over-center position of the septum 50b is dampened both in the forward and rearward direction.

Figure 19:
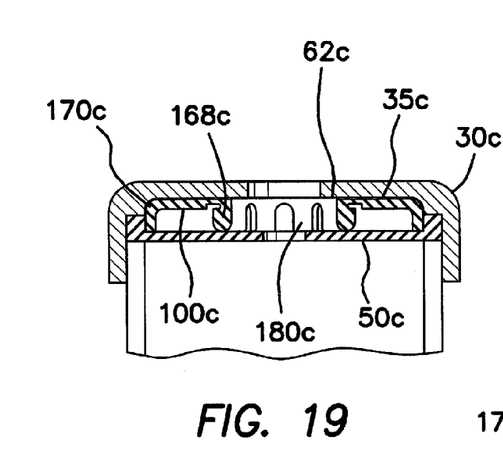
FIG. 19 illustrates a side-section view of a housing according to another aspect of the invention including a ring-shaped segmented projection that is separately formed from the cap.
Figure 20:
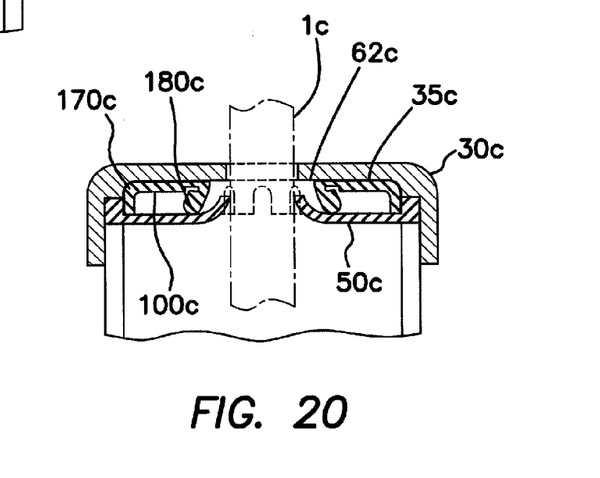
FIG. 20 illustrates a side-section view of the housing of FIG. 19 with an instrument in the working channel and the septum seal in the stretched condition.

Referring to FIGS. 19 and 20, it is appreciated that the ring-shaped annular projection 168c may be formed separately to be located between the septum seal 50c and the proximal wall 62c of cap 30c. In particular, the ring-shaped projection 168c may further comprise a discrete and separate ring 100c that may be assembled between the septum seal 50c and the proximal wall 62c of cap 30c. The ring 102c may cover most of the proximal wall 62c and may be glued, snap fit, or otherwise attached to the proximal wall 62c. The ring 102c may further comprise a wall 170c along an outer diameter of ring 102c. It is appreciated that whether the projections 68b, 168c are formed as part of the cap or separately to be located between the septum seal and the cap, the projections 68b, 168c perform similar functions as described above.

Figure 21:
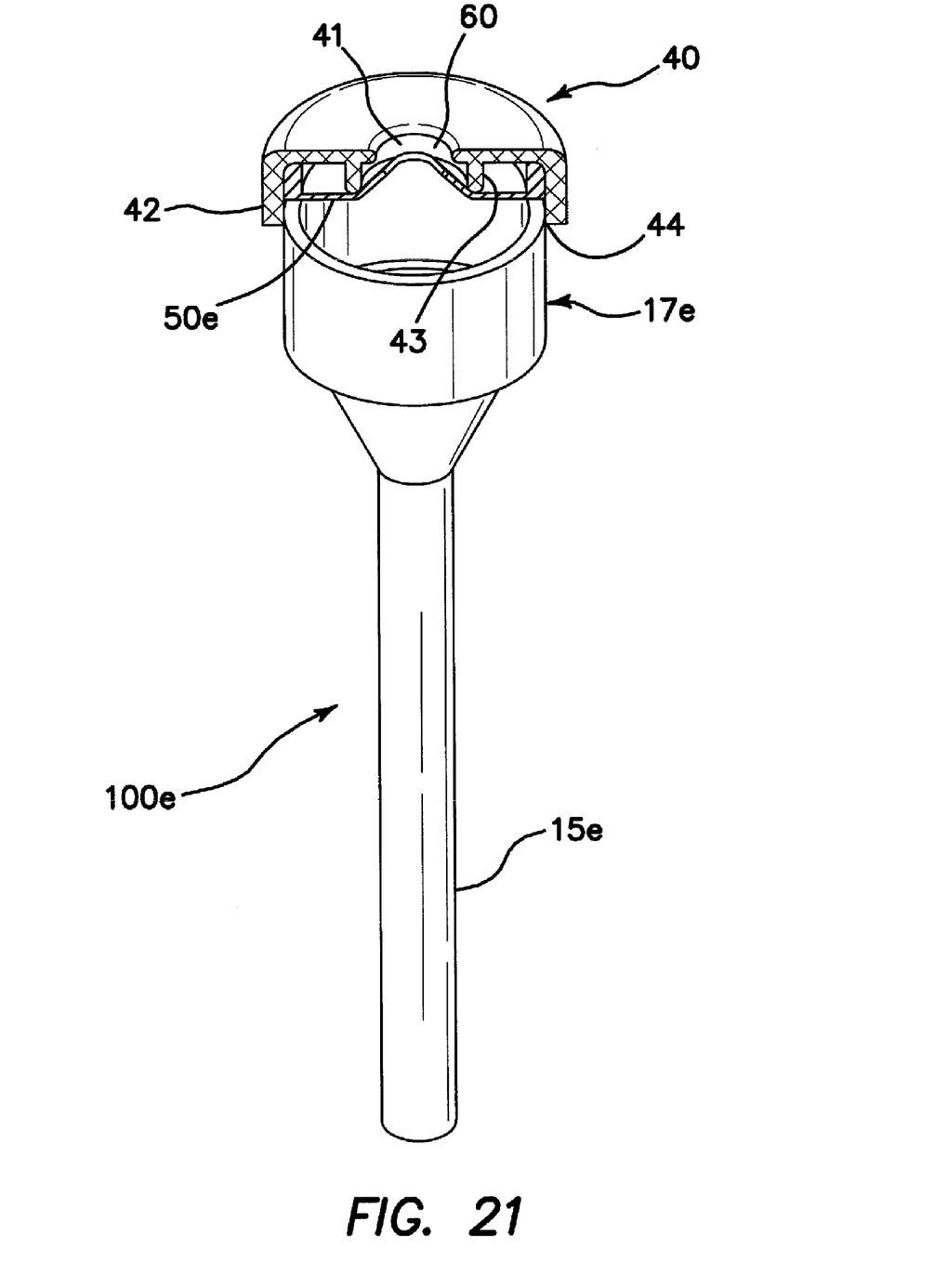
FIG. 21 is a perspective section view of a trocar according to another aspect of the invention where the cap and the ring-shaped projection are formed as a one-piece elastomeric component.
Figure 22:
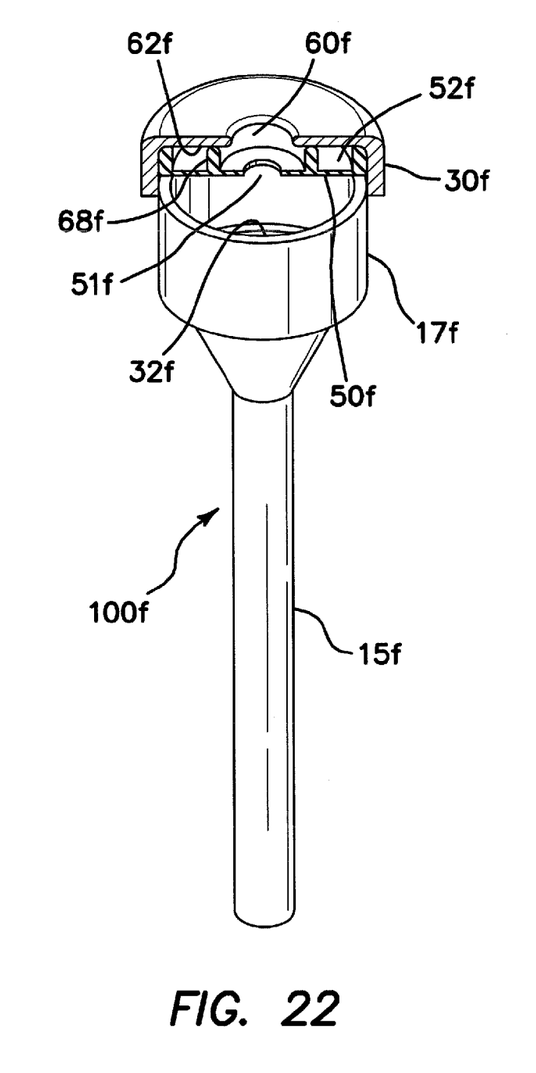
FIG. 22 is a perspective section view of a trocar according to another embodiment of the invention.
Figure 23:
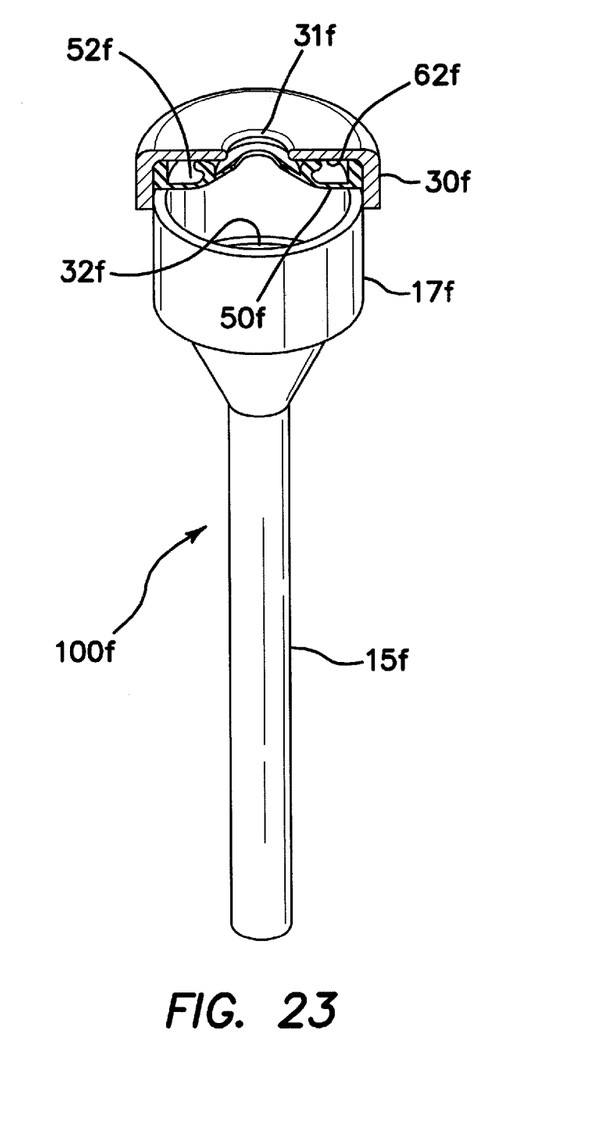
FIG. 23 illustrates the septum seal of the trocar of FIG. 22 when an instrument is within the working channel of the trocar.
Figure 24:
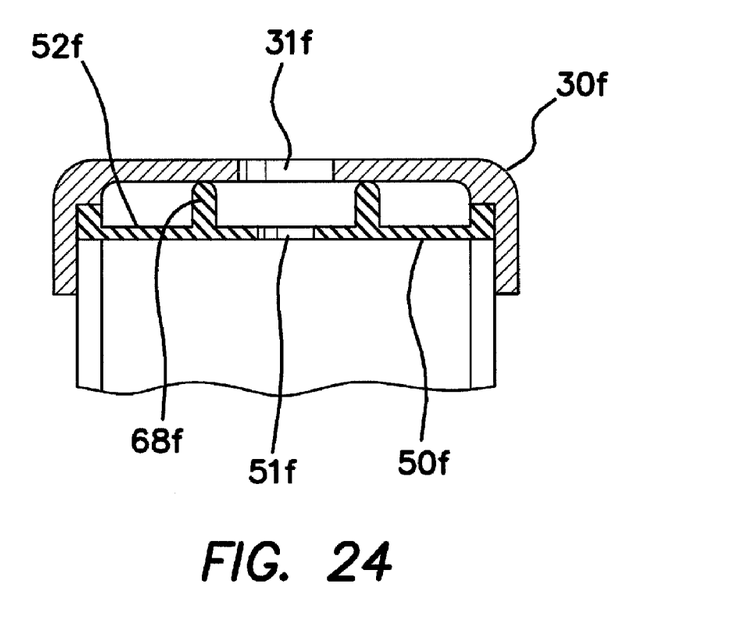
FIG. 24 illustrates a side-section view of a housing of the trocar of FIG. 22 with no instrument in the working channel and the septum seal in a relaxed condition.
Figure 25:
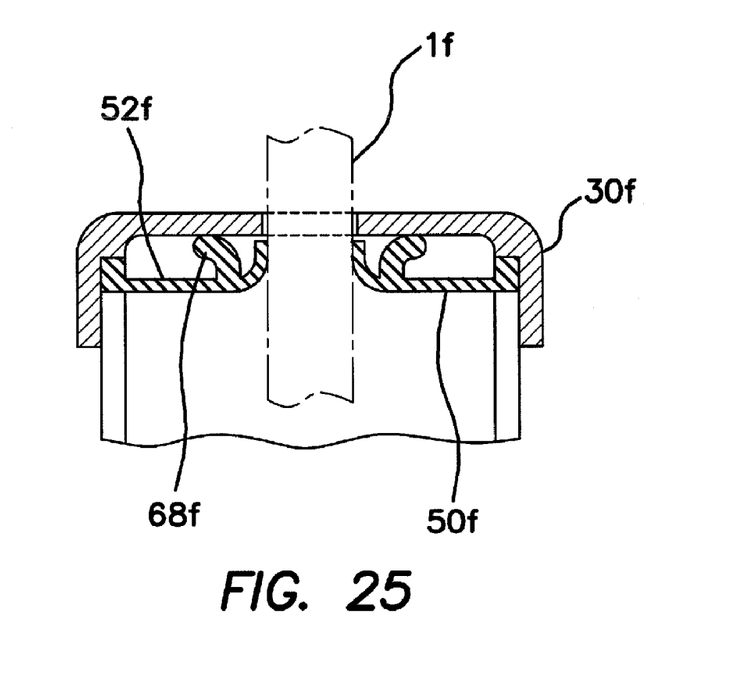
FIG. 25 illustrates a side-section view of the housing of the trocar of FIG. 22 with an instrument in the working channel and the septum seal in a stretched condition.

FIG. 21 illustrates another aspect of the invention where a seal-housing cap 40 is made of an elastomeric material and a ring-shaped projection 43 is formed as part of the elastomeric cap 40 so that they are formed as one piece. The elastomeric cap 40 and ring-shaped projection 43 may be fitted onto or into a seal housing 17e of an access device 100e and form a fluid tight connection without the need for additional assembly.

The ring-shaped projections can also take other forms as illustrated in FIGS. 22-25, where there is shown a surgical access device 100f in accordance with another aspect of the invention. The access device 100f comprises a cannula 15f and a seal housing 17f operatively connected to a proximal end of the cannula 15f to form a seal around a surgical instrument inserted through the surgical access device 100f. The seal housing 17f further comprises a seal-housing cap 30f operatively attached at the proximal end of the seal housing 17f and a septum seal 50f to maintain a fluid tight barrier when an instrument 1f is inserted within a working channel 32f of the access device 10f. With this aspect, the septum seal 50f includes a ring-shaped projection 68f extending axially proximally from a surface 52f toward an inner surface 62f of the cap 30f so as to create an annular recess 60f. That is, the projection 68f may be formed as an integral flange on the septum seal 50f and that is aligned with a cap center orifice 31f. The cap 30f is preferably formed of a rigid material, and the projection 68f is formed from an elastomeric material including polyisoprene, latex, silicone, neoprene, vinyl and the like. The hardness of the material may be adjusted to provide specific attributes. In another aspect, the projection 68f may be bonded to or insert-molded with surface 52f of septum seal 50f. It is appreciated that whether the projection is integrally formed, bonded, or insert-molded with the septum seal 50f, the projection 68f of the invention eliminates inversion of the septum seal during instrument positioning and withdrawal. Furthermore, the elastomeric material of the ring-shaped projection 68f prevents excessive wear or possible damage to the delicate septum seal 50f, and facilitates the over-center positioning of the septum as an instrument transitions from a forward to a rearward condition during insertion and withdrawal.

It will be understood that many other modifications can be made to the various disclosed embodiments without departing from the spirit and scope of the invention. For these reasons, the above description should not be construed as limiting the invention, but should be interpreted as merely exemplary of preferred embodiments.

The invention claimed is:

1. A trocar adapted to form a seal around a surgical instrument, comprising:
    a cannula having an axis extending between a proximal end and a distal end;
    a housing having a proximal wall and forming with the cannula a working channel sized and configured to receive the instrument;
    a septum seal disposed in the housing and extending transverse to the axis of the cannula across the working channel, the septum seal having a normal state when the instrument is absent from the working channel and a stretched state when the instrument is being withdrawn from the working channel;
    portions of the proximal wall of the housing defining an orifice sized and configured to receive the instrument into the working channel; and
    an elastomeric ring-shaped projection extending axially distally between the proximal wall and the septum seal, the ring-shaped projection having an axial length adapted to deform to prevent inversion and binding of the septum seal and the orifice upon withdrawal of the surgical instrument,
    wherein the proximal wall comprises a holding feature and wherein the elastomeric ring-shaped projection is fixed and coupled to the holding feature.

2. The trocar of claim 1, wherein the septum seal is prevented from reaching the orifice in the proximal wall of the housing when the instrument is withdrawn.

3. The trocar of claim 1, further comprising a zero closure valve disposed in the housing distally of the septum seal.

4. The trocar of claim 3, wherein the zero closure valve is a double duck-bill valve.

5. The trocar of claim 1, wherein the ring-shaped projection is bonded to the holding feature.

6. The trocar of claim 1, wherein the ring-shaped projection is insert-molded to the holding feature.

7. The trocar of claim 1, wherein the ring-shaped projection is integrally formed with the holding feature.

8. The trocar of claim 1, wherein the ring-shaped projection is compressively fitted onto the holding feature.

9. The trocar of claim 1 wherein the housing is formed of a rigid material.

10. The trocar of claim 1, wherein the ring-shaped projection is formed of an elastomeric material such as natural or synthetic rubber including at least one of gel, silicone, soft thermoplastics, polyvinyl chloride (PVC), urethane, thermoplastic elastomers, Kraton®, latex, pellethane, monoprene, neoprene, and polyisoprene.

11. The trocar of claim 10, wherein the ring-shaped projection facilitates over-center positioning of the septum seal during insertion and removal of the surgical instrument.

12. The trocar of claim 1, wherein the elastomeric material of the ring-shaped projection prevents excessive wear on the septum seal.

13. A trocar adapted to form a seal around a surgical instrument, comprising:
    a cannula having an axis extending between a proximal end and a distal end;
    a housing having a proximal wall and forming with the cannula a working channel sized and configured to receive the instrument;
    a septum seal disposed in the housing and extending transverse to the axis of the cannula across the working channel, the septum seal having a surface opposing the proximal wall of the housing, the septum seal having a normal state when the instrument is absent from the working channel and a stretched state when the instrument is being withdrawn from the working channel;
    portions of the proximal wall of the housing defining an orifice sized and configured to receive the instrument into the working channel; and
    wherein the proximal wall further comprises a stand-off formed therewith and an elastomeric ring-shaped projection fixed and joined to the stand-off, the elastomeric ring-shaped projection extending axially distally between the proximal wall and the septum seal and having a dimension adapted to deform to prevent inversion and binding of the septum seal and the orifice upon withdrawal of the surgical instrument.

14. The trocar of claim 13, wherein the septum seal is prevented from reaching the orifice in the proximal wall of the housing when the instrument is withdrawn.

15. The trocar of claim 13, wherein the ring-shaped projection is bonded to the stand-off of the proximal wall.

16. The trocar of claim 13, wherein the ring-shaped projection is insert-molded to the stand-off of the proximal wall.

17. The trocar of claim 13, wherein the ring-shaped projection is compressively fitted onto the stand-off of the proximal wall.

18. The trocar of claim 13, wherein the housing is formed of a rigid material.

19. The trocar of claim 13, wherein the ring-shaped projection is formed of an elastomeric material such as natural or synthetic rubber including at least one of gel, silicone, soft thermoplastics, polyvinyl chloride (PVC), urethane, thermoplastic elastomers, Kraton®, latex, pellethane, monoprene, neoprene, and polyisoprene.

20. The trocar of claim 19, wherein the elastomeric material of the ring-shaped projection prevents excessive wear on the septum seal.

* * * * *